United States Patent [19]

Jon et al.

[11] 4,086,816

[45] May 2, 1978

[54] METHOD AND APPARATUS FOR DISTINGUISHING STRESS WAVE EMISSIONS FROM MECHANICAL NOISE

[75] Inventors: Min-Chung Jon, Cranbury; Charles Andrew Keskimaki, Plainsboro; Sotirios John Vahaviolos, West Windsor Township, Mercer County, all of N.J.

[73] Assignee: Western Electric Co., Inc., New York, N.Y.

[21] Appl. No.: 808,833

[22] Filed: Jun. 22, 1977

[51] Int. Cl.² .................................................. G01N 29/00
[52] U.S. Cl. ........................................................ 73/587
[58] Field of Search ................. 73/584, 587, 588, 590, 73/592, 593, 88 R

[56] References Cited

U.S. PATENT DOCUMENTS

| 3,858,439 | 1/1975 | Nakamura | 73/587 |
| 3,965,726 | 6/1976 | Vahaviolos | 73/587 |
| 4,004,456 | 1/1977 | Vahaviolos | 73/587 |
| 4,006,625 | 2/1977 | Davis | 73/587 |

Primary Examiner—Richard C. Queisser
Assistant Examiner—John P. Beauchamp
Attorney, Agent, or Firm—D. J. Kirk

[57] ABSTRACT

Signals emanating from a weld are detected during the post weld period and excursions of the detected signal above a predetermined threshold are counted. Simultaneously, an envelope of the signal is developed and excursions thereof above the threshold are also counted. A ratio of the signal excursion count to the envelope excursion count is formed. The ratio so formed is compared to known ranges of ratio values to determine whether the detected signal is mechanical noise or a stress wave emission signal.

11 Claims, 9 Drawing Figures

METHOD AND APPARATUS FOR DISTINGUISHING STRESS WAVE EMISSIONS FROM MECHANICAL NOISE

BACKGROUND OF THE INVENTION

1. Field of the Invention

This invention relates to a method for the real-time, non-destructive evaluation of welds, thermocompression bonds or the like by stress-wave emission techniques. In particular, a method is disclosed for distinguishing between mechanical noise and stress wave emission signals detected during welding, bonding or like operations.

2. Description of the Prior Art

The evaluation of adhesion bonds, welds or the like using real-time, non-destructive stress wave emission techniques is well known. For instance, U.S. Pat. No. 3,965,726 which issued on June 29, 1976 to S. J. Vahaviolos and is assigned to the instant assignee, describes the real-time evaluation of welds by monitoring emitted stress waves. Stress Wave Emissions (SWE's) may be defined as elastic waves which are characterized by low amplitude, short duration and fast rise time signals which are propagated in a structure as a result of an applied stress. As described in the aforementioned patent, the SWE energy emitted from the weld area during the solid-to-liquid phase transformation and the liquid-to-solid phase transformation are measured. The stress wave energy emitted during the liquid-to-solid phase transformation is subtracted from the stress wave energy emitted during the solid-to-liquid phase transformation and that value is compared with a predetermined value to determine the acceptability of the weld.

Another application relating to the use of SWE evaluation techniques is described in U.S. Pat. No. 4,004,456 which issued on Jan. 25, 1977 to S. J. Vahaviolos and is assigned to the instant assignee. In that patent, SWE energy is measured during the compression phase of an adhesion bond and that value is compared to a predetermined substantially linear relationship between the emitted stress wave energy and the strength of the particular adhesion bond being formed.

The foregoing techniques have been quite successful in determining the quality or the strength of bonds. However, at times, undesirable noise vibrations are caused by the head of the welding tool or bonder or the like. Such mechanical vibrations result in relatively high amplitude oscillating signals which last for an extended period of time and which are incorrectly interpreted by the stress wave detection equipment as SWE signals, causing incorrect evaluation and attendant loss of acceptable product.

Accordingly, there is a need for a method to distinguish between SWE signals and undesirable mechanical noise.

SUMMARY OF THE INVENTION

The instant invention provides an effective method of determining whether a detected signal is a mechanical noise or a SWE signal. The method comprises the steps of (a) counting the number of excursions of the detected signal above a preset threshold, (b) counting the number of excursions above a preset threshold made by the envelope of the detected signal, (c) forming a ratio of the count in step (a) with the count in step (b), and (d) comparing the ratio so formed with known ranges of ratio values to determine whether the detected signal is mechanical noise or a SWE signal.

Apparatus to implement the foregoing method is comprised of means for counting the number of excursions made by both the detected signal and the envelope thereof above a preset threshold. A means is provided to form a ratio of the counts of the signal excursions to the envelope excursions. A further comparing means is also provided to compare the ratio so formed with a predetermined ratio to determine whether the detected signal is a mechanical noise signal or a SWE signal.

DETAILED DESCRIPTION OF THE PREFERRED EMBODIMENT

The instant invention wil be described in relation to the real-time, non-destructive evaluation of a weld. However, it will be understood that such description is exemplary only and is for the purposes of exposition and not for the purposes of limitation. It will be readily appreciated that the instant inventive concept is equally applicable to distinguishing mechanical noise from SWE signals in other operations involving bonding, testing or the like where a mechanical force is applied to a bonding site to determine the quality (strength) of the bond. For example, the present concepts could be implemented during the pressure relief phase of a thermocompression bonding operation to distinguish SWE signals from mechanical noise.

The welding process involves the steps of mechanically holding articles to be welded together, melting the parts at their common interface, causing molten material to flow, and resolidifying the molten volume. The volume where the melting occurs is generally called the molten-resolidification zone or weld nugget, while the region where grain structure modification takes place is generally called the heat affected zone. The required interfacial heat can be supplied in a number of different ways, one of which is by capacitor discharge welding where a pulse of high current is passed across the weld part interface.

Figure 1:
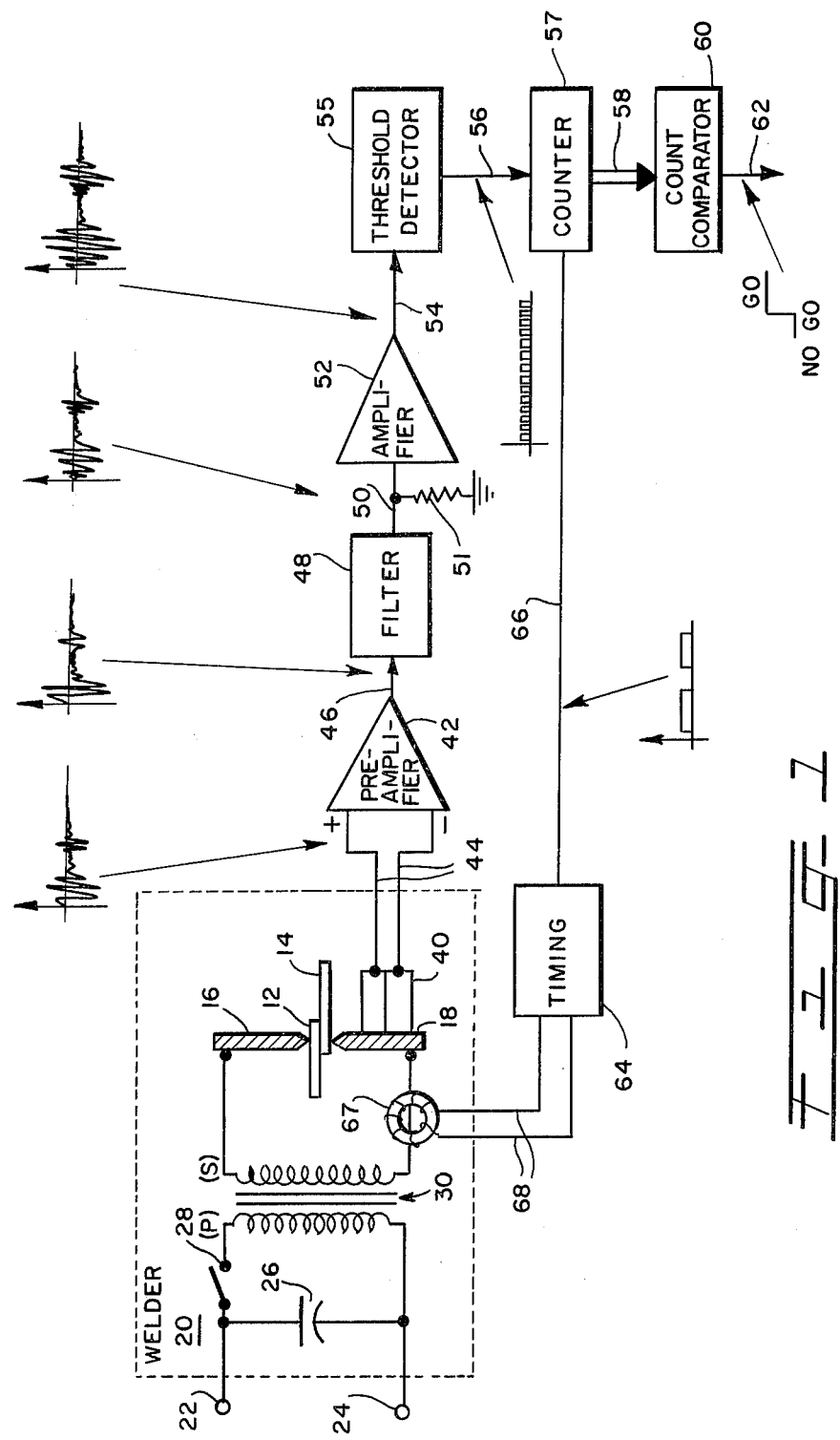
FIG. 1 is a block diagram of a prior art SWE evaluation apparatus.

Referring to FIG. 1, which depicts a known SWE evaluation apparatus, a pair of overlapping articles 12 and 14 comprising the same or different material are positioned to be welded together between electrodes 16 and 18 of a capacitive discharge welding 20. When a power source (not shown) is connected to a pair of terminals 22 and 24 of the welding 20, a capacitor 26 becomes charged. The closure of a switch 28 discharges the capacitor 26 through a primary winding (P) of a transformer 30, causing a pulse of current to be delivered to the secondary winding (S) of the transformer, to the electrodes 16 and 18, and across the weld part interface. The capacitor 26 should be of sufficient size to deliver a pulse of current which will melt and plastically deform the weld area at the interface of the articles 12 and 14.

Stress waves emitted from the weld area during both the weld pulse and post weld intervals are detected by a piezoelectric differential transducer 40 (hereinafter referred to as sensor 40) of the weld evaluation apparatus. Sensor 40 is shown as being mechanically coupled to electrode 18, but could also be coupled to electrode 16 or either one of the articles 12 and 14.

The signals which are detected by the sensor 40 comprise waves which are: (a) generated by other electrical components proximate the welding apparatus; (b) generated in the articles 12 and 14, the electrodes 16 and 18, or the sensor 40 due to non-transient factors such as temperature and strain variations; and (c) stress waves due to microcracking, comprising bulk and surface waves, emanating from the weld nugget in the articles 12 and 14 during the weld cycle.

Whenever a phase transformation occurs in the weld nugget, energy is released in the form of stress waves, which waves, in turn, excite the sensor 40. Depending on the wave dampening at the interfaces, the travelling mechanical stress impulses will cause the sensor 40 to provide output voltage changes which are almost proportional to the amplitude of the pulses. Because of the low amplitude of the SWE signals, it is advantageous to provide for good transmission of the mechanical wave or amplification of the sensor's output voltage.

As shown in FIG. 1, the sensor 40 is connected to a low noise preamplifier 42 over a pair of leads 44—44. The preamplifier 42 should be of a design having a sensitivity which is preferably in the range of 1–4$\mu$ V but can include a sensitivity beyond this range, as for example, 6$\mu$V. The output from the preamplifier 42 is transmitted over a lead 46 to a band-pass filter 48 which has a band-pass that falls at least partially within the natural frequency of the sensor 40, but which falls outside the range of noise frequencies generated by other components proximate the system. Filter 48 is preferbly a commercially available, fifth order, or higher, high-pass filter. A resistor 51 is preferably connected to a line 50 which connects the output of the filter 48 to the input of an amplifier 52 to match the impedance input thereof. The amplifier 52 is of a design which advantageously has a fast slewing rate, such as, for example, a commercially available model 715 operational amplifier.

The output of the amplifier 52 is transmitted over a lead 54 to a threshold detector 55 which will provide an output pulse on a lead 56 each time the detected signal crosses above a preset threshold. A counter 57 receives the pulses transmitted on the lead 56 where the pulses are counted and forwarded, via lead 58, to a comparator 60 which compares the count to a predetermined acceptable value below which is indicated a poor quality (low strength) bond and generates a go or no-go signal on a lead 62.

Properly timed trigger pulses are generated by a timing circuit 64 and forwarded to the counter 57 over lead 66. The timing circuit 64 is responsive to a detecting means 67, positioned about the secondary winding (S), which detects the presence of a weld current pulse as the capacitor 26 discharges, and generates a signal in response via leads 68—68. The detecting means 67 may take various forms, for example, a toroidal coil may be advantageously used.

Accordingly, in the foregoing prior art apparatus shown in FIG. 1, the signals emanating from the bond site as the nugget melt is formed as well as during the post weld cooling period are detected by the sensor 40 and forwarded to threshold detector 55 via the preamplifier 42, filter 48 and the amplifier 52. The threshold detector 55 will provide an output pulse for each positive excursion made by the signal above a predetermined threshold. The pulses will be counted by the counter 57 during predetermined intervals based upon enable signals generated by the timing circuit 64. The count during the selected interval is forwarded to the comparator 60 which compares the interval count to a previously determined acceptable count for that particular interval. The comparator 60 based upon the comparison will output a signal on the lead 62 indicative of either an acceptable or unacceptable weld.

Such a technique has been found to be most effective in the real time non-destructive testing of welds or the like. However, occasionally, harmonics of high energy mechanical noise, not related to weld microcracking, are detected and pass through the filter 48. Even though the low-frequency portion of the noise spectrum is removed by using a high frequency sensor and a high-pass filter, a large amount of energy is still left in the frequency band of the SWE signals. Such mechanical noise may be caused by loose or defective bonding electrodes or other equipment operating proximate to the stress wave sensor 40. The prior art apparatus as shown in FIG. 1 will count all signal excursions passing through a predetermined threshold. Accordingly, the harmonics of the mechanical noise signals will be counted as a SWE count (see FIGS. 3A and 3B) resulting in a no-go condition even though the weld may have been acceptable. Thus, the stress wave emission measuring equipment could erroneously indicate that good product was unacceptable.

Applicants have overcome the foregoing problem by first recognizing that mechanical noise signals have a high amplitude and decay over a relatively long period of time, as shown in the post weld period portion of FIG. 3B, while SWE signals due to microcracking are of relatively low amplitude, short duration and fast rise time (sometimes referred to as packets of pulses) as shown in the post weld period portion of FIG. 3E.

In order to distinguish between these two types of signals, applicants form an envelope 76 (see FIG. 3B or 3E) of the detected signal and count the number of excursions through a predetermined threshold 77 made by the envelope. Simultaneously, the excursions above the same threshold 77 made by the detected signals are also counted. A ratio of the signal excursion count to the envelope excursion count is then made and is compared to a predetermined acceptable ratio. If the ratio so formed falls in the range at or above the predetermined acceptable ratio, it is an indication that the detected signal is mechanical noise while if the ratio is in a range at or below the acceptable ratio, the detected signal is a SWE signal which is caused by microcracking. If the detected signal is a SWE signal, then the threshold excursions made by the detected signals may be used to determine the quality of the bond. If the ratio so formed is a mechanical noise signal the product must be retested after readjusting the welding apparatus to eliminate the source of the unwanted mechanical vibrations.

FIGS. 3A to 3G show various waveforms which depict signals generated during the illustrative weld evaluation process. FIG. 3A is a curve of the weld current versus time. The time during which the current is on is referred to the weld or melting period. The current is shown as being off during the post weld or resolidification period. FIGS. 3B to 3D depict signals generated when the detected signal is mechanical noise, while FIGS. 3E to 3G show signals generated when the detected signals are SWE signals. The signals shown during the weld period in FIGS. 3B and 3E are illustrative of the type of signals detected during the melting of the materials being welded. The instant inventive concept is illustrated by the signals detected and generated during the post weld period.

Figure 3:
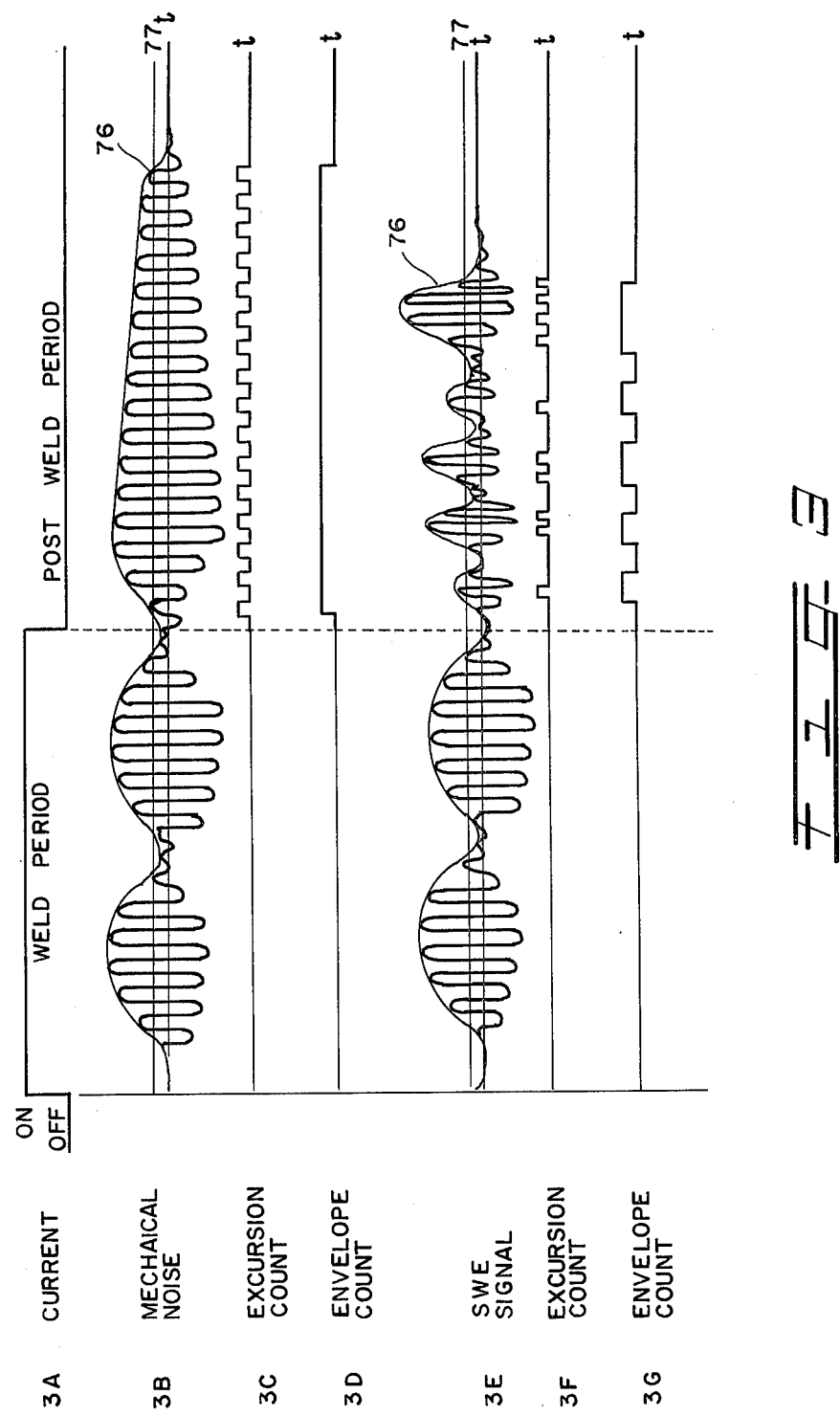
FIGS. 3A to 3G depict electrical waveforms occurring during the instant SWE evaluation process.

The signals are actually generated at a much higher rate than shown in FIG. 3 and the ratios formed would normally be much higher. However, for purposes of clarity and for explanation, signals of lower frequency are used.

During the post weld period of FIG. 3B, the signal shown is mechanical noise detected by the sensor 40. It should be noted that the mechanical noise signal has a relatively high amplitude and decays slowly over an extended period of time and the envelope 76 of the signal takes on a similar character. The number of excursions made by the detected signal and by the envelope 76 above the threshold 77 are counted. For example, FIG. 3C shows 16 signal excursion counts while FIG. 3D shows that the envelope has but a single excursion count resulting in a 16:1 ratio between the two counts. In contrast, when a SWE signal due to microcracking is detected by the sensor 40, a signal as shown during the post weld period of FIG. 3E will result. That waveform is comprised of packets or clusters of relatively low amplitude and fast rise time signals having an envelope 76. The excursion count above threshold 77 of the detected SWE signals and the envelope thereof are counted as shown in curves of FIGS. 3F and 3G, respectively. The ratio of the two counts being relatively low, 2:1, is an indication that the detected signals are, in fact, stress wave emission signals. Accordingly, a low ratio of the excursions above the threshold 76 of the detected signal to envelope thereof is indicative of SWE signals while a high ratio is indicative of mechanical noise signals.

Figure 2:
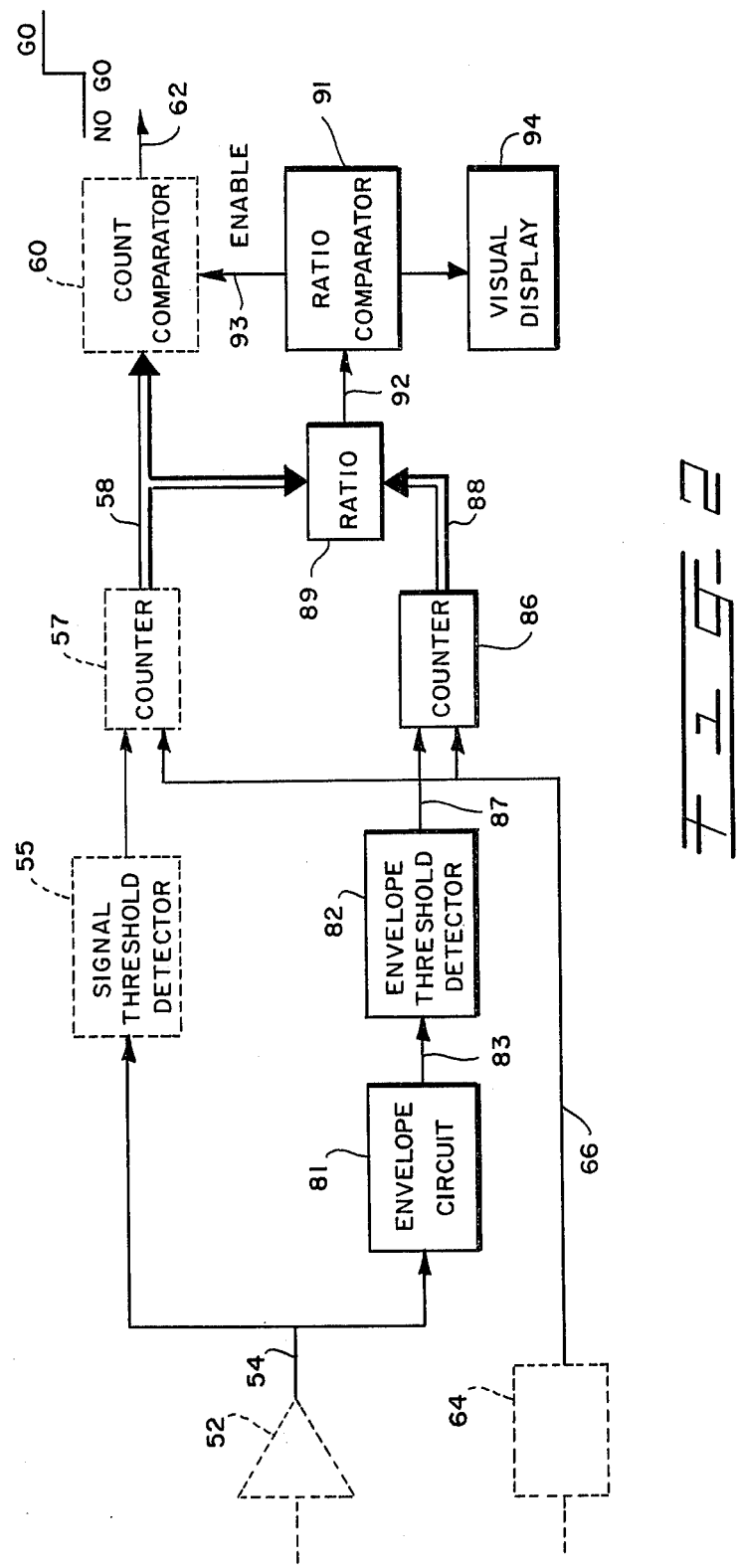
FIG. 2 is a block diagram of a modified SWE evaluation apparatus illustrative of the instant inventive concepts.

Apparatus which is used to implement the above-described method is set forth in FIG. 2 which shows equipment placed after amplifier 52 and the timing circuit 64 shown in FIG. 1. The apparatus shown in FIG. 1 is shown in phantom in FIG. 2 and retains the same numerical designation, while additional apparatus is shown in FIG. 2 with solid lines. In FIG. 2, the detected signal on the lead 54 is shown as dividing into two paths. The first or upper path is substantially as shown in FIG. 1 with the serial connection of the threshold detector 55, the counter 57 and the comparator 60 connected to the output 54 of amplifier 52. Additionally, the output 54 is connected to an envelope circuit 81 to form the envelope of the detected signal, which envelope signal is forwarded to an envelope threshold detector 82 over a lead 83. The envelope threshold detector 82 provides an output pulse for each positive excursion of the envelope 76 above the threshold 77 (see FIGS. 3B and 3E). The output pulses from the envelope threshold detector 82 are forwarded to, and counted by, a second counter 86 over a lead 87.

A timing pulse generated by the timing circuit 64 is forwarded to the input of counters 57 and 86 to enable the counters to count the pulses generated by the signal threshold detector 55 and the envelope threshold detector 82, respectively, during a predetermined window or period of time. The accumulated count in the counters 57 and 86 is outpulsed over paths 58 and 88, respectively, to a ratio forming circuit 89 which will form the ratio of the signal excursion count to the envelope excursion count and forward that ratio to a ratio comparator 91 via a connection 92. The ratio comparator 91 compares the received ratio to a predetermined, empirically developed ratio. If the ratio received from the ratio forming circuit 89 is equal to or less than the predetermined ratio, an enable signal is forwarded to signal count comparator 60 over lead 93 to permit the go or no-go output to be presented on lead 62. However, if the ratio is greater than the predetermined ratio value, a signal is forwarded to a visual display circuit 94 over a lead 96 to provide an audible and/or a visual indication of a high ratio which is indicative that the detected input signal is mechanical noise. The welding equipment may then be checked for loose parts, adjusted and the weld and tests rerun.

The parameters used to implement the instant concepts will vary depending on the particular operation. For the instant illustrative welding process, a ratio of 100:1 was found to be satisfactory in distinguishing between mechanical noise and SWE signals. The maximum amplitude of the SWE signal at the output of the amplifier 52 was approximately 150 mv and the maximum amplitude of the noise signals at the same point was about 400 mv. As hereinbefore indicated, the value of the threshold 76 may be the same in the signal threshold detector 55 and the envelope threshold detector 82. However, the threshold value 76 may be set between 70 to 80 mv in the detector 55 and approximately 105 mv in the detector 82.

Although the instant method has been found most useful in distinguishing SWE signals from mechanical noise, it is not so limited. This method could be applied wherever signals characterized by low amplitude, short duration and fast rise time are generated in an environment which may contain undesirable high energy noise comprised of signals of high amplitude that extend for relatively long periods of time.

What is claimed is:

1. A method of determining, during an operation, whether a detected signal is mechanical noise or a stress wave emission signal, comprising the steps of:
    (a) counting the number of excursions of the detected signal above a preset threshold;
    (b) counting the number of excursions above a preset threshold made by an envelope of the detected signal;
    (c) forming a ratio of the count of step (a) to the count of step (b); and
    (d) comparing said ratio with known ranges of ratio values to determine whether the detected signal is mechanical noise or a stress wave emission signal.

2. The method as set forth in claim 1 wherein the operation is welding of articles and the detected signal emanates from the weld area during the post weld period.

3. The method as set forth in claim 1 wherein the operation is thermocompression bonding and the detected signal emanates from the bond area during the pressure relief interval.

4. The method as set forth in claim 2 wherein the predetermined ratio value is 100:1.

5. A real time, non-destructive method of determining the quality of a weld by counting the number of excursions above a preset threshold made by a signal detected at the weld site during the post weld site period and comparing said count to a predetermined count to determine the quality of the weld, the method further comprising the steps of:
    generating an envelope of the detected signal;
    counting the number of excursions made above a preset threshold by said envelope;

forming a ratio of the signal excursion count to the envelope excursion count; and comparing the ratio so formed with predetermined ranges of ratios to determine whether the detected signal is mechanical noise or a stress wave emission signal and provide an output indicative of the type of signal detected.

6. Apparatus for determining, during an operation, whether a detected signal is mechanical noise or a stress wave emission signal, comprising:

means for counting the number of excursions above a first preset threshold made by the detected signal;

means for counting the number of excursions above a second preset threshold made by an envelope of the detected signal;

means for forming a ratio of the excursion count of the detected signal to the excursion count of the envelope thereof; and means for comparing said ratio with known ranges of ratio values to determine whether the detected signal is mechanical noise or a stress wave emission signal.

7. The apparatus as set forth in claim 6, which further comprises:

means for enabling both counting means to count excursions during the same time period.

8. The apparatus as set forth in claim 6, wherein the operation is welding of articles and the detected signal emanates from the weld site during the post weld period.

9. The apparatus as set forth in claim 6 wherein the operation is themocompression bonding and the detected signal emanates from the bond area during the pressure relief interval.

10. The apparatus as set forth in claim 8 wherein the predetermined ratio value is 100:1.

11. The apparatus as set forth in claim 6 wherein the operation is welding and is further characterized by:

means for comparing the detected signal excursion count to a predetermined signal excursion count to determine the quality of the weld and provide an output indicative of said quality upon receipt of an enable signal from said ratio comparing means when the detected signal is a stress wave emission signal.

* * * * *